United States Patent [19]

Mannheimer et al.

[11] Patent Number: 5,218,962
[45] Date of Patent: Jun. 15, 1993

[54] MULTIPLE REGION PULSE OXIMETRY PROBE AND OXIMETER

[75] Inventors: Paul D. Mannheimer, Belmont; D. Christopher Chung, Pleasanton; Carl Ritson, San Jose, all of Calif.

[73] Assignee: Nellcor Incorporated, Hayward, Calif.

[21] Appl. No.: 685,414

[22] Filed: Apr. 15, 1991

[51] Int. Cl.⁵ .................................................. A61B 5/00
[52] U.S. Cl. ................................. 128/633; 128/666; 356/41
[58] Field of Search ........................... 128/633–634, 128/664–666; 356/41

[56] References Cited

U.S. PATENT DOCUMENTS

| 4,890,619 | 1/1990 | Hatschek | 128/633 |
| 4,927,264 | 5/1990 | Shiga et al. | 128/633 |
| 4,938,218 | 7/1990 | Goodman et al. | 128/666 |
| 5,024,226 | 6/1991 | Tan | 128/633 |

FOREIGN PATENT DOCUMENTS

| 2216804 | 10/1989 | United Kingdom | 128/634 |
| 8901310 | 2/1989 | World Int. Prop. O. | 128/680 |

OTHER PUBLICATIONS

A Non-Invasive Reflectance Oximeter as a Useful Monitor in ICU, Y. Shimada, et al., Equipment, Monitoring, and Engineering Technology IV, Anesthesiology, V71, No. 3A, Sep. 1989, A366.

Skin Reflectance Pulse Oximetry: In Vivo Measurements from the Forearm and Calf, Y. Mendelson, PhD, et al., Journal of Clinical Monitoring, vol. 7, No. 1, Jan. 1991, pp. 7–12.

Design and Evaluation of a New Reflectance Pulse Oximeter Sensor, Y. Mendelson, PhD, et al., Medical Instrumentation vol. 22, No. 4, Aug. 1988, pp. 167–173.

Primary Examiner—Lee S. Cohen
Assistant Examiner—Robert L. Nasser, Jr.
Attorney, Agent, or Firm—Townsend and Townsend Khourie and Crew

[57] ABSTRACT

A first light emitting element directs light through a first region of tissue, a second light emitting element directs light through a second region of tissue that is spatially distinct from the first region of tissue, and a photodetector detects light traveling through the first and second regions. First and second oxygen saturation values are calculated from the amount of light detected from the first and second regions of tissue, respectively. A difference calculating unit calculates a difference value which represents how much the first oxygen saturation value differs from the second oxygen saturation value, and a comparator compares the difference value to a threshold value. A threshold indicating signal is provided when the difference value has a selected mathematical relationship (e.g., less than or equal) to the threshold value.

12 Claims, 2 Drawing Sheets

MULTIPLE REGION PULSE OXIMETRY PROBE AND OXIMETER

BACKGROUND OF THE INVENTION

This invention relates to pulse oximetry devices and, more particularly, to an improved fetal pulse oximetry probe and oximeter.

Pulse oximeters are typically used to measure various blood characteristics including arterial blood oxygen saturation and pulse rate. Pulse oximetry devices typically comprise a non-invasive probe which passes light through a portion of the patient's tissue where blood perfuses the tissue, and which photoelectrically senses the absorption of light in the tissue. The detected light is then used to determine the characteristic of interest.

In plethysmography (e.g., pulse rate and amplitude) and pulse oximetry (blood oxygen saturation), the light passed through the tissue is selected to be of one or more wavelengths that are absorbed by the blood. The amount of light passed through the tissue varies in accordance with the amount of blood and blood constituents in the tissue. For measuring blood oxygen saturation, such sensors are provided with light sources at two or more wavelengths and a photodetector that is adapted to operate at those wavelengths in accordance with known techniques for measuring blood oxygen saturation. See, e.g., U.S. Pat. No. 4,653,498 issued to New, Jr., et al. incorporated herein by reference.

Pulse oximetry probes generally fall into two categories. Transmissive pulse oximetry probes shine light through opposed blood perfused tissue surfaces, such as a finger or ear, emitting and detecting light on opposite sides of the tissue. Transflectance probes both emit light into and detect light from the same side of the blood perfused tissue.

Pulse oximeters may be used to measure fetal blood oxygen saturation in utero during labor and delivery. Since the presenting part of a fetus (usually the head) does not offer opposed tissue surfaces for transmissive pulse oximetry, transflectance probes are often used. However, transflectance pulse oximetry probes are quite susceptible to inaccuracies caused by shunting of light between the emitter and detector, i.e., light which travels from the probe's emitter to the detector but which bypasses the blood perfused tissue. Shunting of light may occur for many reasons.

FIG. 1 shows a transflectance pulse oximetry probe 10 comprising a light emitter 14 and light detector 18 disposed within a housing 22. Probe 10 is disposed in close proximity to a body 26 which includes blood perfused tissue layer 30, bloodless tissue layer 32, and skin 34. Path 1 shows light which fully penetrates the blood perfused layer 30. Now assume that probe 10 is in poor contact with skin 34, and that there is extraneous matter 38 such as hair, mucus, etc., disposed between probe 10 and skin 34. When the probe is in poor contact with the skin, light may be directly reflected from the top surface of the skin or piped through the extraneous matter as shown by path 2. Alternatively, the light may scatter below the surface of skin 34 but may not travel deep enough to penetrate blood perfused layer 30. Instead, the light travels through layer 32 as shown by path 3. The depth uniformity and/or location of layer 32 is typically affected by local vasoconstriction, excessive force applied to the back surface of the probe (which locally exsanguinates blood from the tissue beneath the probe), site-to-site variations of the distance to the blood perfused layer or the lack of blood vessels in the region. Thus, unless the placement of the surface probe is well controlled in an environment free of excessive applied force and other light shunting causes, accuracy of the calculated saturation will be suspect.

Pulse oximetry in the fetal environment is challenged by the above factors, and is further complicated by the fact that the intrauterine sensor site is remote and cannot be directly observed. Consequently, knowledge about the quality of the site and the sensor to tissue contact is either difficult or simply unavailable, and the oximetry data is sometimes unreliable.

SUMMARY OF THE INVENTION

The present invention is directed to a pulse oximetry system which reliably monitors blood characteristics, such as oxygen saturation and pulse rate, in an unknown environment by sensing the blood characteristics at two or more unique sites. If the measurements from the multiple sites agree (within a predetermined margin), the probability that the true value of the parameter has been obtained is higher than if a single measurement is taken. The invention is particularly useful for monitoring blood characteristics of a fetus during labor and delivery. A device constructed according to the present invention generally comprises one or more pulse oximetry probes which passes electromagnetic radiation (e.g., light) through a plurality of unique regions of tissue. A sensor associated with each region of tissue detects the amount of light passing through the tissue, and an instrument calculates the oxygen saturation level within each of the multiple regions from the sensor signals. Since the saturation values derived from the sensor signals from the multiple regions will be equivalent only when the radiation passes through similar environments, the agreement of multiple saturation values may be used as corroborating evidence of their accuracy and reliability.

In one embodiment of the present invention, a first light emitting element directs light through a first region of tissue, a second light emitting element directs light through a second region of tissue that is unique from the first region of tissue, and a photodetector detects light traveling through the first and second regions. A calculating unit calculates oxygen saturation independently for each region. A difference calculating unit calculates a difference value which represents how much the oxygen saturation of the first region of tissue differs from the oxygen saturation of the second region of tissue, and a comparator compares the difference value to a threshold value. A threshold indicating signal is provided when the difference value has a selected mathematical relationship (e.g., less than or equal) to the threshold value. Depending on the value of the threshold indicating signal, the final oxygen saturation value is either displayed as a function of the first and second oxygen saturation values, or is not displayed at all.

DETAILED DESCRIPTION OF THE PREFERRED EMBODIMENTS

Figure 1:
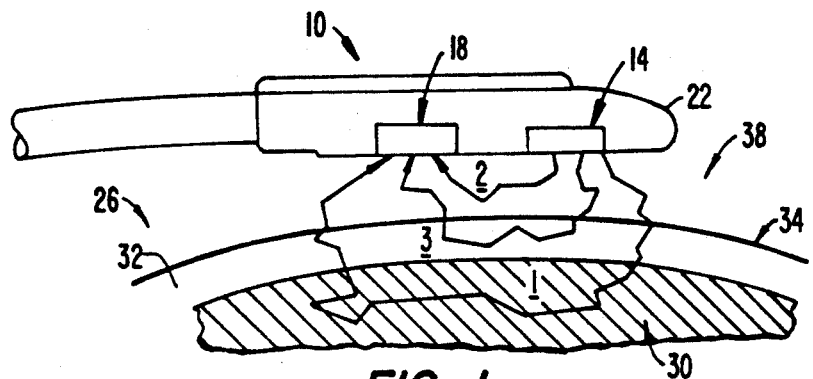
FIG. 1 is a cross-sectional diagram of a pulse oximetry probe showing light transmission through various layers of tissue.
Figure 2:
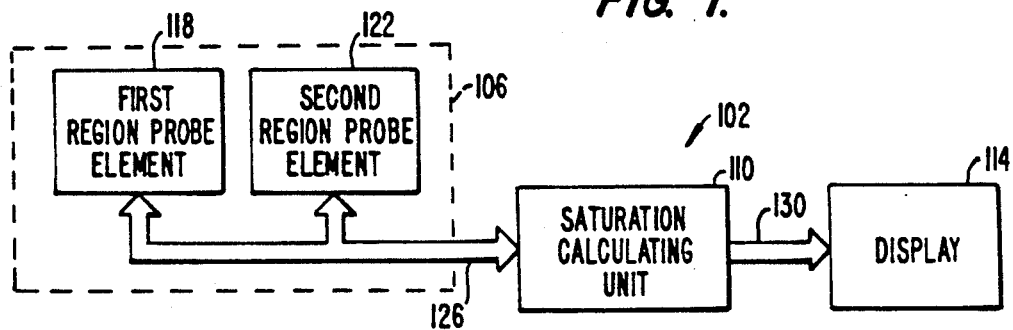
FIG. 2 is a conceptual block diagram of a particular embodiment of a pulse oximeter according to the present invention.

FIG. 2 is a conceptual block diagram of an improved pulse oximeter 102 according to the present invention. Pulse oximeter 102 includes a pulse oximetry probe 106, a saturation calculating unit 110, and a display 114. Probe 106 comprises a first region probe element 118 for electromagnetically (e.g., optically) probing a first region of tissue and a second region probe element 122 for electromagnetically probing a second region of tissue that is distinct from the first region of tissue. First region probe element 118 and second region probe element 122 communicate with saturation calculating unit 110 over a bus 126. Saturation calculating unit 110 processes the data from first region probe element 118 and second region probe element 122 and calculates an oxygen saturation ($SpO_2$) value for the probed regions and a confidence value which indicates the degree of reliability of the oxygen saturation value. The calculated oxygen saturation value and confidence value are communicated to display 114 over a bus 130 so that the calculated values may be displayed on an appropriate monitor.

Figure 3:
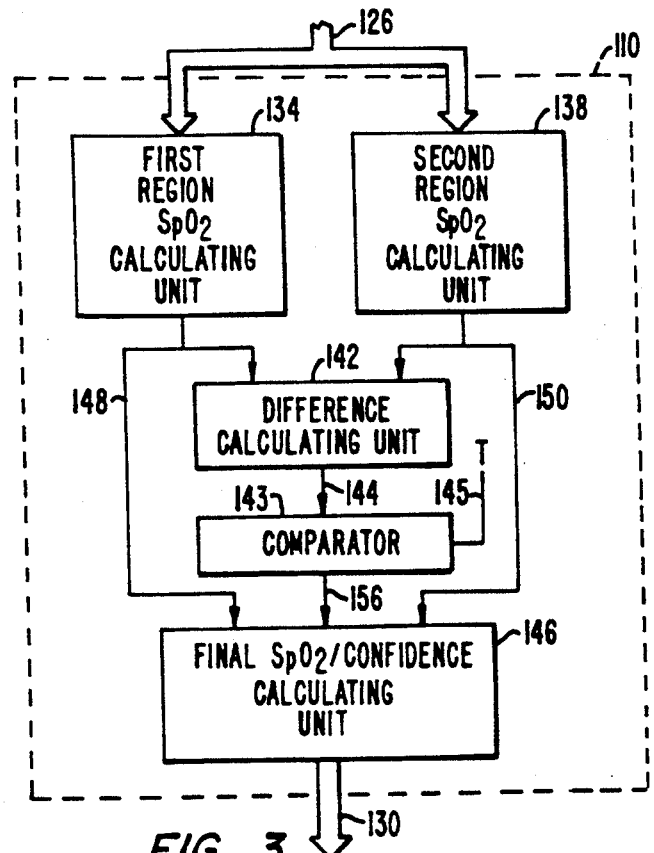
FIG. 3 is a conceptual block diagram of a particular embodiment of the saturation calculating unit of FIG. 2.

FIG. 3 is a conceptual block diagram of saturation calculating unit 110. Data from first region probe element 118 is communicated to a first region $SpO_2$ calculating unit 134 which calculates an oxygen saturation value for the tissue probed by first region probe element 118. Similarly, data from second region probe element 122 is communicated to a second region $SpO_2$ calculating unit 138 which calculates an oxygen saturation value for the tissue probed by second region probe element 122. The calculated oxygen saturation values are communicated to a difference calculating unit 142 and to a final $SpO_2$/confidence calculating unit 146 over buses 148 and 150, respectively. Difference calculating unit 142 calculates a difference value which represents the difference between the two calculated oxygen saturation values. The difference value is communicated to a comparator 143 over a bus 144. Comparator 143 compares the difference value to a selected threshold value $\delta$ received over a bus 145 and provides a threshold indicating signal on a bus 156 to final $SpO_2$/confidence calculating unit 146 when the difference value has a selected mathematical relationship (e.g., less than or equal) to the threshold value $\delta$. Final $SpO_2$/confidence calculating unit 146 calculates a final oxygen saturation value and a confidence value in response to the oxygen saturation values received over buses 148 and 150 and the threshold indicating signal 1 received over bus 156. The calculated values are then communicated to bus 130.

Figure 4:
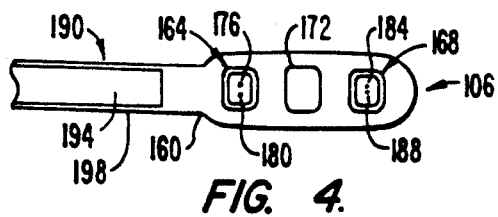
FIG. 4 is a front view of a particular embodiment of a pulse oximetry probe according to the present invention.

FIG. 4 is a front view of a particular embodiment of pulse oximetry probe 106. Pulse oximetry probe 106 comprises a resilient housing 160 in which is embedded an electromagnetic radiation directing unit 164, an electromagnetic radiation directing unit 168, and an electromagnetic radiation detecting unit 172. In this embodiment, housing 160 is formed of black silicone rubber so that the sensors conform to the shape of the site as well as to allow for better mechanical independence of the two probed regions. Radiation directing unit 164 comprises a first light emitting diode (LED) 176 and a second LED 180. LED 176 emits red light having a wavelength of approximately 660 nanometers (a red LED), and LED 180 emits infrared light having a wavelength of approximately 900 nanometers (infrared LED). Similarly, radiation directing unit 168 includes a red LED 184 and an infrared LED 188. Electromagnetic radiation detector 172 is a standard photodetector which may be shielded by a faraday shield to prevent electromagnetic interference. In this embodiment, the spacing between radiation directing units 164, 168 and radiation detector 172 is approximately 10 mm center-to-center for both sides. Radiation directing units 164, 168 and radiation detector 172 are coupled to wires (not shown) which form bus 126.

Also affixed to housing 160 is a handle 190 which functions as an insertion aid. Handle 190 comprises, e.g., a 0.02 inch thick by 0.10 inch wide by 11 inch long stainless steel stiffener 194 which is enclosed by a tube 198 which may comprise heat shrink tubing. In general, stiffener 194 is shaped as a substantially flat rod for allowing bending in a first direction (e.g., toward the regions to be probed) while resisting bending in a second direction (e.g., laterally).

Figure 5:
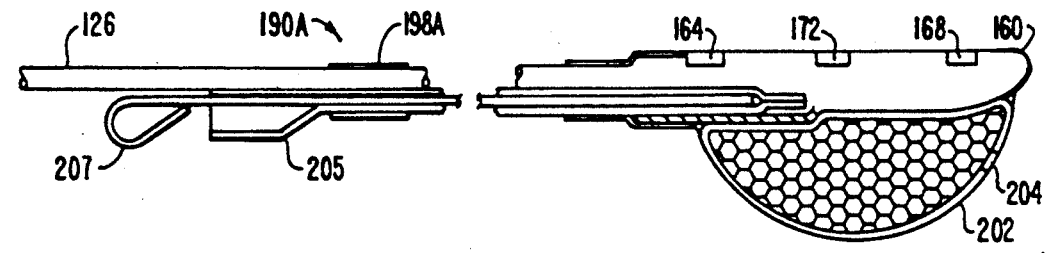
FIG. 5 is a side view of an alternative embodiment of the pulse oximetry probe according to the present invention.

FIG. 5 is a side view of an alternative embodiment of the pulse oximetry probe according to the present invention. In this embodiment, an optional biasing bladder 202 made, e.g., of open-celled polyurethane foam may be disposed on the back of housing 160. Bladder 202 includes an opening 204 which allows the bladder to be deflated and flattened prior to placement of the probe adjacent to the fetus. Bladder 202 then expands as it fills with fluid for biasing electromagnetic directing units 164, 168 and electromagnetic detector 172 toward the tissue regions to be probed. In this embodiment, opening 204 is approximately 0.050", although the size of the opening may be varied to produce the desired rate of expansion of bladder 202.

Also shown in FIG. 5 is a modified handle 190A which comprises a substantially flat guide tube 205 which, together with the wires which form bus 126, is enclosed by a tube 198A which again may comprise heat shrink tubing. A removable stiffener 207 is disposed within guide tube 205 before shrinking tube 198A and then removed after tube 198A is shrunk. Stiffener 207 ensures that handle 190A has the desired property of allowing bending toward the regions to be probed while resisting lateral bending. Stiffener 207 is preferably used during manufacture of the handle 190 shown in FIG. 4 for the same purpose.

Figure 6:
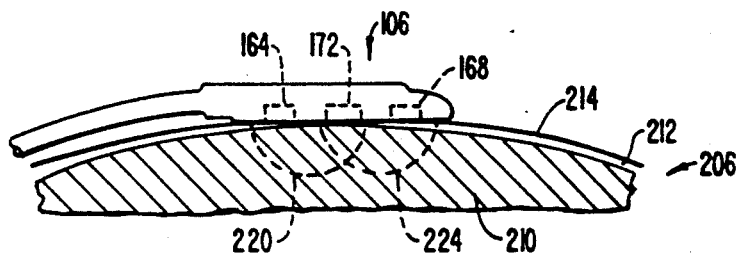
FIG. 6 is a diagram showing the pulse oximetry probe of FIG. 4 in close proximity to a segment of tissue.
Figure 7:
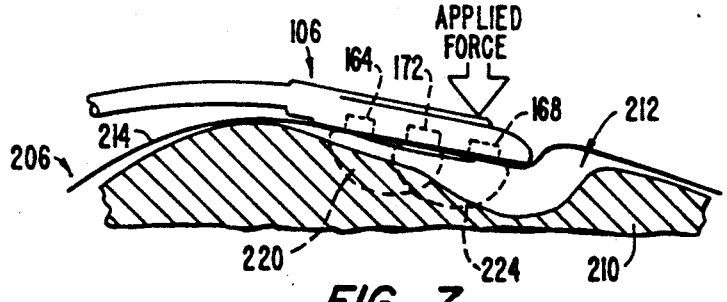
FIG. 7 is a diagram showing a pulse oximetry probe in close proximity to a segment of tissue wherein one of the tissue regions probed is heavily exsanguinated.

FIGS. 6 and 7 illustrate the operation of probe 106 under different circumstances. FIG. 6 shows probe 106 evenly disposed in close proximity to a segment of tissue 206 comprising a blood perfused layer 210, bloodless layer 212, and skin 214. Electromagnetic radiation directing unit 164 directs red and infrared radiation through a first region 220 of tissue, and electromagnetic radiation directing unit 168 directs red and infrared radiation through a second region 224 of tissue. Since the light path through the blood in regions 220 and 224 are substantially the same, saturation values independently calculated from the two regions will nominally agree with one another, thus indicating reliable data.

FIG. 7 shows the operation of probe 106 when force against tissue 210 by probe 160 exsanguinates the tissue, thereby expanding bloodless layer 212. In this case, the electromagnetic radiation directed through region 220 passes through much more blood perfused tissue than the electromagnetic radiation directed through region 224. Thus, the calculated oxygen saturation values become different from each other, indicating less reliable data.

Oxygen saturation values are calculated from the red and infrared data in a conventional manner. See, e.g., U.S. Pat. No. 4,653,498 referred to in the Background of the Invention. The conventional method of time multiplexing the red and infrared channels is expanded to include two more channels. Scaling of the appropriate gain and LED drive levels is handled in the same manner as is done for a conventional two channel systems. The gain within the demultiplexing filter chain may be doubled, since the time-averaged signal level from each of the four channels is half that of a two channel system.

The two measurements taken by the probe of this invention are used to compute a confidence value. The confidence value may be a function of the difference between the two measurements, optical signal quality, correlation between the optical pulse rate and a measured ECG signal, or other factors. The confidence value may be used to determine whether and in what manner to display the blood characteristic measurement. In the preferred embodiment, the confidence value is calculated and used as follows.

If $Sat_1$ and $Sat_2$ represent the oxygen saturation values calculated for regions 220 and 224, respectively, then the final saturation value is calculated as follows:

If $|Sat_1 - Sat_2| \leq \delta$ then Displayed Saturation $= \frac{1}{2}(Sat_1 + Sat_2)$ If $|Sat_1 - Sat_2| > \delta$ then Displayed Saturation = Not Available where $\delta$ is an empirically derived threshold value received over bus 145. In this embodiment, $\delta \approx 10$ sat points. In addition, a confidence value is computed and displayed on an 8 LED segment analog bar graph. The confidence value may be calculated as a function of optical pulse amplitude, the agreement between optically derived heart rate and ECG derived heart rate and/or other factors.

Alternatively, the difference between the measured 1 saturation values may be used to derive a weighting factor used together with the other factors discussed above to compute the confidence value.

Figure 8:
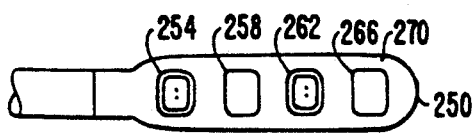
FIG. 8 is a front view of an alternative embodiment of the pulse oximetry probe according to the present invention.
Figure 9:
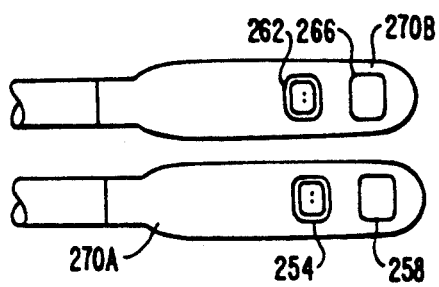
FIG. 9 is a front view of an alternative embodiment of the pulse oximetry probe of FIG. 8.

While the above is a complete description of a preferred embodiment of the present invention, various modifications may be employed. For example, the role of electromagnetic directing units 164, 168 and detector 172 may be reversed. That is, a single electromagnetic directing unit may be disposed between two (or more) detecting units. FIG. 8 shows another embodiment in which probe 250 having a first electromagnetic radiation directing unit 254, a first electromagnetic radiation detecting unit 258, a second electromagnetic radiation directing unit 262, and a second electromagnetic radiation detecting unit 266 disposed in a housing 270. In this embodiment, electromagnetic directing unit 254 and electromagnetic detecting unit 258 are used to probe the first region of tissue, and electromagnetic directing unit 262 and electromagnetic detecting unit 266 are used for probing a second region of tissue. FIG. 9 shows an alternative embodiment of the probe shown in FIG. 8. In this embodiment, electromagnetic directing unit 254 and electromagnetic detecting unit 258 are disposed in a first housing 270A, and electromagnetic directing unit 262 and electromagnetic detecting unit 226 are disposed in a second housing 270B.

Other emitter/detector configurations are possible. Also, in the case of multiple emitters and multiple detectors, each detector may operate with more than one emitter or emitter pair. In addition, the emitter/detector combinations may be mounted in separate probe housings, and the separate probes may be connected to one or more oximeter monitors.

Consequently, the scope of the invention should not be limited except as described in the claims.

What is claimed is:

1. A pulse oximeter comprising:
   light emitting means for directing light through first and second unique regions of tissue;
   detecting means for detecting the light directed through the first and second regions of tissue;
   wherein the light emitting means and the detecting means are disposed in close proximity to each other;
   saturation calculating means, coupled to the detecting means, for calculating a first oxygen saturation value from the amount of light detected from the first region of tissue and a second oxygen saturation value from the amount of light detected from the second region of tissue;
   difference calculating means, coupled to the saturation calculating means for calculating a difference value which represents how much the first oxygen saturation value differs from the second oxygen saturation value;
   threshold comprising means, coupled to the difference calculating means, for comparing the difference value to a threshold value; and
   threshold indicating means, coupled to the threshold comparing means, for providing a threshold indicating signal when the difference value is not greater than the threshold value.

2. The probe according to claim 1 wherein the light emitting means comprises:
   a first light emitting element for directing light through the first region of tissue;
   a second light emitting element for directing light through the second region of tissue.

3. The probe according to claim 2 wherein the detecting means comprises:
   a first photodetector disposed in close proximity to the first light emitting element and spaced apart therefrom for detecting the light directed through the first region of tissue; and
   a second photodetector disposed in close proximity to the second light emitting element and spaced apart therefrom for detecting the light directed through the second region of tissue.

4. The probe according to claim 3 wherein the first light emitting element, the second light emitting element, the first photodetector, and the second photodetector are disposed in a common housing.

5. The probe according to claim 3 wherein the first light emitting element and the first photodetector are disposed in a first housing, and wherein the second light emitting element and the second photodetector are disposed in a second housing.

6. The probe according to claim 4 further comprising placement means, coupled to the housing, for placing the first light emitting element, the second light emitting element, the first photodetector, and the second photodetector in close proximity to the first and second regions of tissue.

7. The probe according to claim 6 wherein the placement means comprises an elongated handle having a first end attached to the housing.

8. The probe according to claim 7 wherein the handle is formed for allowing bending in a first direction and for resisting bending in a second direction.

9. The probe according to claim 8 wherein the handle comprises a substantially flat first rod coupled to the housing.

10. The pulse oximeter according to claim 1 further comprising displayed saturation calculating means, coupled to the detecting means and to the threshold indicating means, for calculating a displayed saturation value when the difference value is not greater than the threshold value and for inhibiting the display of the displayed saturation value when the difference value is greater than the threshold value.

11. A method of determining a characteristic of blood comprising the steps of:

directing electromagnetic radiation through a first region of tissue;

detecting the electromagnetic radiation from the first region of tissue;

calculating a first blood oxygen saturation value from the amount of electromagnetic radiation detected from the first region of tissue;

directing electromagnetic radiation through a second region of tissue, the second region of tissue being unique from the first region of tissue and in close proximity to the first region of tissue;

detecting the electromagnetic radiation from the second region of tissue;

calculating a second blood oxygen saturation value from the amount of electromagnetic radiation detected from the second region of tissue;

calculating a difference value which represents how much the first blood oxygen saturation value differs from the second blood oxygen saturation value;

comparing the difference value to a threshold value; and providing a threshold indicating signal when the difference value is not greater than the threshold value.

12. The method according to claim 11 further comprising the steps of:

calculating a displayed saturation value when the difference value is not greater than the threshold value; and inhibiting the display of the displayed saturation value when the difference value is greater than the threshold value.

* * * * *